US010262413B2

(12) United States Patent
Strnad et al.

(10) Patent No.: US 10,262,413 B2
(45) Date of Patent: Apr. 16, 2019

(54) WORK LAYER IMAGING AND ANALYSIS FOR IMPLEMENT MONITORING, CONTROL AND OPERATOR FEEDBACK

(71) Applicant: THE CLIMATE CORPORATION, San Francisco, CA (US)

(72) Inventors: Michael Strnad, Delavan, IL (US); Roger Koch, Pekin, IL (US); Dale Koch, Tremont, IL (US)

(73) Assignee: THE CLIMATE CORPORATION, San Francisco, CA (US)

( * ) Notice: Subject to any disclaimer, the term of this patent is extended or adjusted under 35 U.S.C. 154(b) by 0 days.

(21) Appl. No.: 15/572,289

(22) PCT Filed: May 6, 2016

(86) PCT No.: PCT/US2016/031201
§ 371 (c)(1),
(2) Date: Nov. 7, 2017

(87) PCT Pub. No.: WO2016/182906
PCT Pub. Date: Nov. 17, 2016

(65) Prior Publication Data
US 2018/0114305 A1  Apr. 26, 2018

Related U.S. Application Data

(60) Provisional application No. 62/159,058, filed on May 8, 2015.

(51) Int. Cl.
| G06T 7/00 | (2017.01) |
| G01N 33/24 | (2006.01) |
| A01B 79/00 | (2006.01) |
| A01C 21/00 | (2006.01) |
| A01C 7/10 | (2006.01) |
| H04N 7/18 | (2006.01) |
| G01V 3/12 | (2006.01) |

(52) U.S. Cl.
CPC ............ G06T 7/001 (2013.01); A01B 79/005 (2013.01); A01C 7/10 (2013.01); A01C 21/00 (2013.01); G01N 33/24 (2013.01); G01V 3/12 (2013.01); H04N 7/185 (2013.01); *G06T 2207/30188* (2013.01)

(58) Field of Classification Search
CPC .......... G06T 7/001; G06T 2207/30188; G01N 21/1765; G01N 21/177; G01N 21/35; G01N 21/3563; G01N 33/24; G01N 33/245; G01V 3/12; A01B 79/00; A01B 79/005; A01C 7/105
See application file for complete search history.

(56) References Cited

U.S. PATENT DOCUMENTS

| 2003/0184747 A1 | 10/2003 | Diekhans et al. ............ 356/300 |
| 2005/0192752 A1 | 9/2005 | Rooney et al. .................... 702/5 |
| 2014/0365084 A1 | 12/2014 | Chan et al. .......... A01C 21/005 |
| 2015/0310633 A1* | 10/2015 | Nelan ..................... G06T 7/408 |
| | | 382/110 |
| 2018/0174291 A1* | 6/2018 | Asada et al. .......... G06T 7/0002 |

FOREIGN PATENT DOCUMENTS

| RU | 2 537 908 C2 | 1/2015 | ............ G01N 33/24 |
| WO | WO 2014/066654 A1 | 5/2014 | ............ A01B 63/00 |

OTHER PUBLICATIONS

International Searching Authority, "Search Report" in application No. PCT/US16/31201, dated Aug. 19, 2016, 16 pages.
Flat Earth Inc., Flat Earth Impulse Radar Solutions, "Services", A Future Farm, http://future-farm.com, dated 2013, 3 pages.

* cited by examiner

*Primary Examiner* — Andrew W Johns
(74) *Attorney, Agent, or Firm* — Hickman Palermo Becker Bingham LLP

(57) ABSTRACT

A soil imaging system having a work layer sensor disposed on an agricultural implement to generate an electromagnetic field through a soil area of interest as the agricultural implement traverses a field. A monitor in communication with the work layer sensor is adapted to generate a work layer image of the soil layer of interest based on the generated electromagnetic field. The work layer sensor may also generate a reference image by generating an electromagnetic field through undisturbed soil. The monitor may compare at least one characteristic of the reference image with at least one characteristic of the work layer image to generate a characterized image of the work layer of interest. The monitor may display operator feedback and may effect operational control of the agricultural implement based on the characterized image.

31 Claims, 6 Drawing Sheets

WORK LAYER IMAGING AND ANALYSIS FOR IMPLEMENT MONITORING, CONTROL AND OPERATOR FEEDBACK

This application is a U.S. National Stage Patent Application filed under 35 U.S.C. § 371 of International Patent Application No. PCT/US2016/031201 filed May 6, 2016, which claims priority to U.S. Provisional Patent Application No. 62/159,058, filed May 8, 2015, the entire contents of all of which are hereby incorporated by reference as if fully set forth herein for all purposes.

BACKGROUND

It is well known that proper and uniform seed trench depth, accurate placement of seed within the seed trench (at the proper depth and proper spacing), good seed-to-soil contact, and minimal crop residue within the seed trench are all critical factors in uniform seed emergence and high yields. Accordingly, various planter improvements have been proposed to achieve each of these factors. While conducting spot checks of the seed trench may help to provide some assurances that these critical factors are being achieved, such spot checks will only identify the conditions at the specific location being checked. Accordingly, there is a need for a system that will image the seed trench to verify and ensure these critical factors are being achieved during planting operations and to enable automatic or remote adjustment of the planter while on-the-go based on the images. There is a similar need for below-soil-surfacing-imaging and control for other types of agricultural implements, including tillage implements, sidedress or in-ground fertilizing implements and agricultural data gathering implements.

DESCRIPTION

Figure 1:
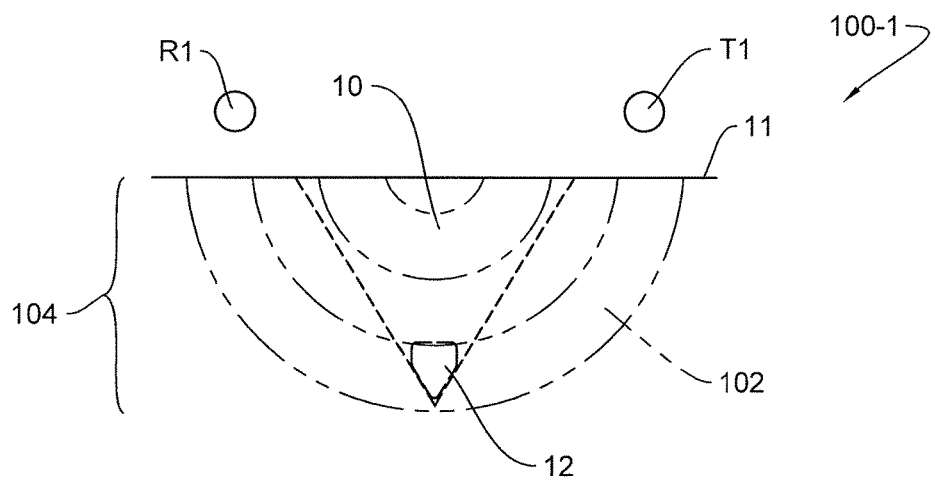
FIG. 1 schematically illustrates one embodiment of a work layer sensor, in elevation view, disposed in relation a seed trench.
Figure 3:
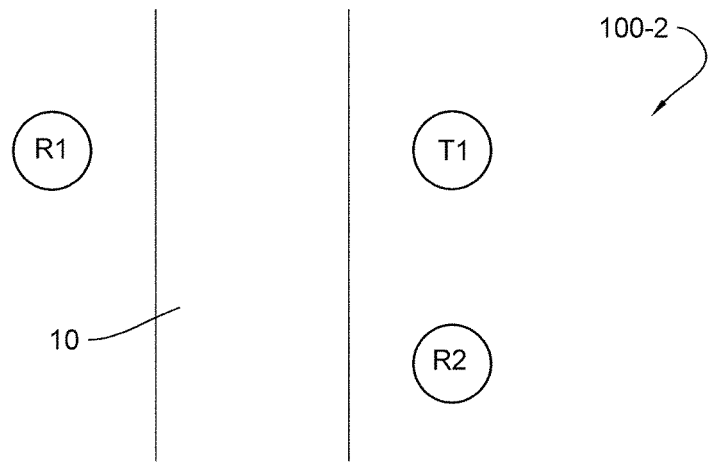
FIG. 3 schematically illustrates another embodiment of a work layer sensor, in plan view, disposed in relation to a seed trench.
Figure 5:
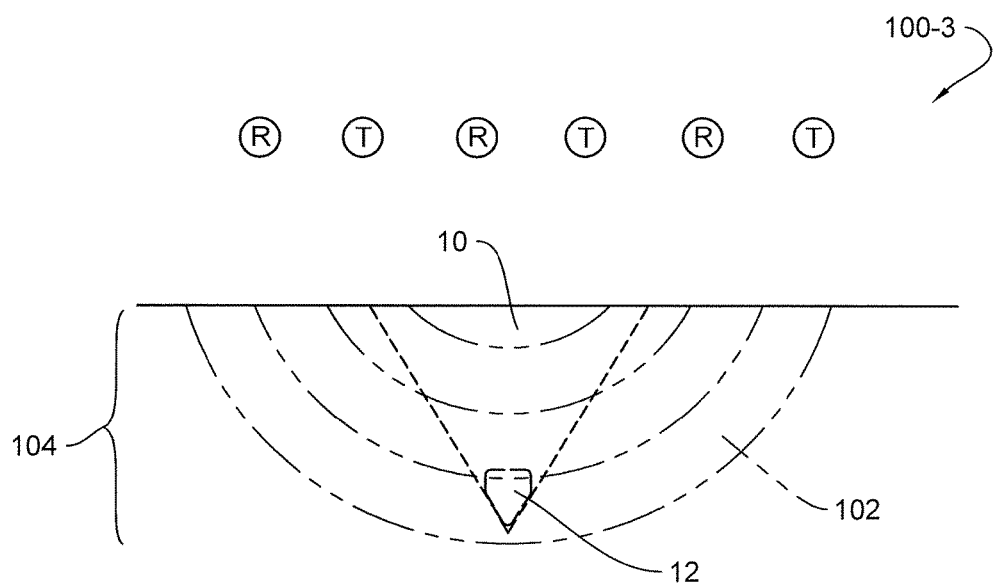
FIG. 5 schematically illustrates another embodiment of a work layer sensor, in elevation view, disposed in relation to a seed trench.

Referring now to the drawings, wherein like reference numerals designate identical or corresponding parts throughout the several views, FIGS. 1, 3 and 5 schematically illustrate alternative embodiments of a work layer sensor 100 to generate a signal or image representative of the soil densities or other soil characteristics throughout a soil region of interest, hereinafter referred to as the "work layer" 104. The representative image or signal generated by the work layer sensor 100 is hereinafter referred to as the "work layer image" 110. In one particular application discussed later, the work layer sensors 100 may be mounted to a planter row unit 200 (FIG. 7) for generating a work layer image 110 of the seed trench as the planter traverses the field. The work layer image 110 may be displayed on a monitor 300 visible to an operator within the cab of a tractor and the planter may be equipped with various actuators for controlling the planter based on the characteristics of the work layer 104 as determined from the work layer image 110.

The work layer sensor 100 for generating the work layer image 110 may comprise a ground penetrating radar system, an ultrasound system, an audible range sound system, an electrical current system or any other suitable system for generating an electromagnetic field 102 through the work layer 104 to produce the work layer image 110. It should be understood that the depth and width of the work layer 104 may vary depending on the agricultural implement and operation being performed.

FIG. 1 is a schematic illustration of one embodiment of a work layer sensor 100-1 disposed in relation to a seed trench 10 formed in the soil 11 by a planter, wherein the seed trench 10 comprises the soil region of interest or work layer 104. In this embodiment, the work layer sensor 100-1 comprises a transmitter (T1) disposed on one side of the seed trench 10 and a receiver (R1) disposed on the other side of the seed trench 10 to produce the electromagnetic field 102 through the seed trench to generate the work layer image 110.

In some embodiments, the work layer sensor 100 may comprise a ground-penetration radar subsurface inspection system such as any of the following commercially available systems: (1) the StructureScan™ Mini HR available from GSSI in Nashua, N.H.; (2) the 3d-Radar GeoScope™ Mk IV coupled to a 3d-Radar VX-Series and/or DX-Series multi-channel antenna, all available from 3d-Radar AS in Trondheim, Norway; or (3) the MALA Imaging Radar Array System available from MALA Geoscience in Mala, Sweden. In such embodiments, the commercially available system may be mounted to the planter or other implement, or may be mounted to a cart which moves with the implement; in either case the system is preferably disposed to capture an image of a work layer in the area of interest (e.g., the seed trench). In some embodiments, the work layer image 110 may be generated from the signal outputs of the work layer sensor 100 using commercially available software such as GPR-SLICE (e.g., version 7.0) available from GeoHiRes International Ltd. located in Borken, Germany.

Figure 2A:
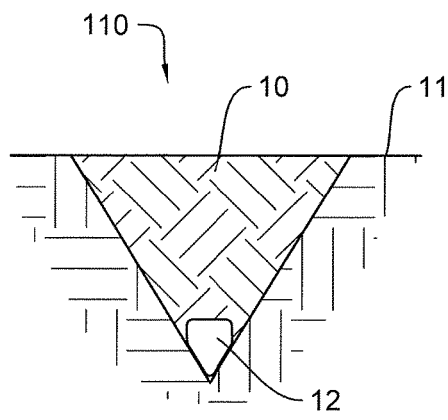
FIGS. 2A-2C are representative examples of work layer images generated by the work layer sensor of FIG. 1.
Figure 2B:
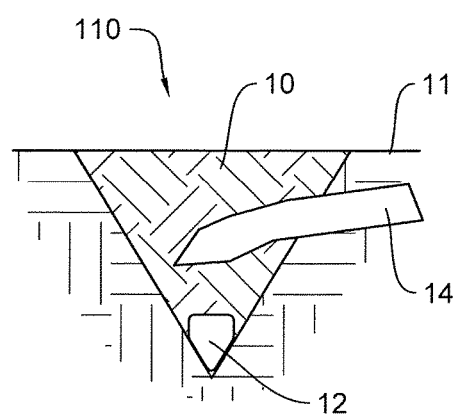
Figure 2C:
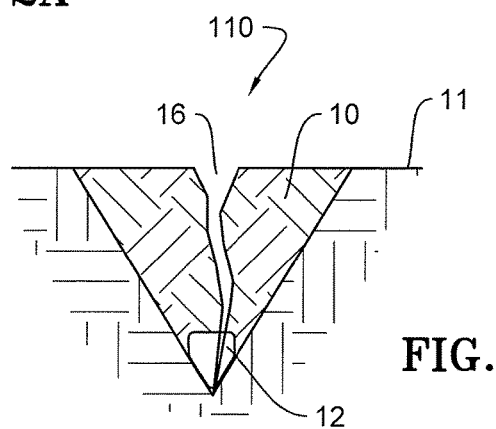

FIGS. 2A-2C are intended to be representative examples of work layer images 110 generated by the work layer sensor 100-1 of FIG. 1 showing various characteristics of the seed trench 10, including, for example, the trench depth, the trench shape, depth of seed 12, the seed depth relative to the trench depth, crop residue 14 in the trench, and the void spaces 16 within the trench. As described in more detail later, the work layer images 110 may be used to determine other characteristics of the work layer 104, including, for example, the seed-to-soil contact, percentage of trench closed, percentage of upper half of trench closed, percentage of lower half of trench closed, moisture of the soil, etc.

Figure 4A:
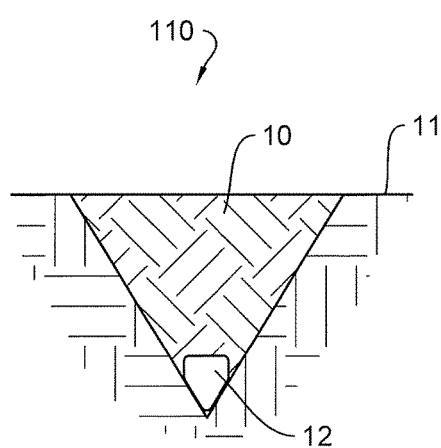
FIG. 4A-4B are representative examples of work layer images generated by the work layer sensor of FIG. 3.
Figure 4B:
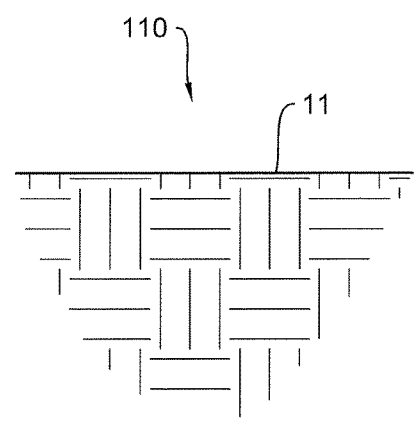

FIG. 3 schematically illustrates, in plan view, another embodiment of a work layer sensor 100-2 disposed with respect to a seed trench 10. In this embodiment, a transmitter (T1) is disposed on one side of the seed trench 10, a first receiver (R1) is disposed on the other side of the seed trench 10, and a second receiver (R2) is disposed adjacent and rearward of the transmitter (T1). FIG. 4A is a representative illustration of the work layer image 110 generated through the trench between the transmitter (T1) and the first receiver (R1)) and FIG. 4B is a representative illustration of the work layer image 110 generated between the transmitter (T1) and the second receiver (R2) providing an image of the undisturbed soil adjacent to the seed trench.

FIG. 5 is an elevation view schematically illustrating another work layer sensor embodiment 100-3 disposed with respect to a seed trench 10. In this embodiment, the work layer sensor 100-3 comprises a plurality of transmitter and receiver pairs disposed above and transverse to the seed trench 10.

Figure 6:
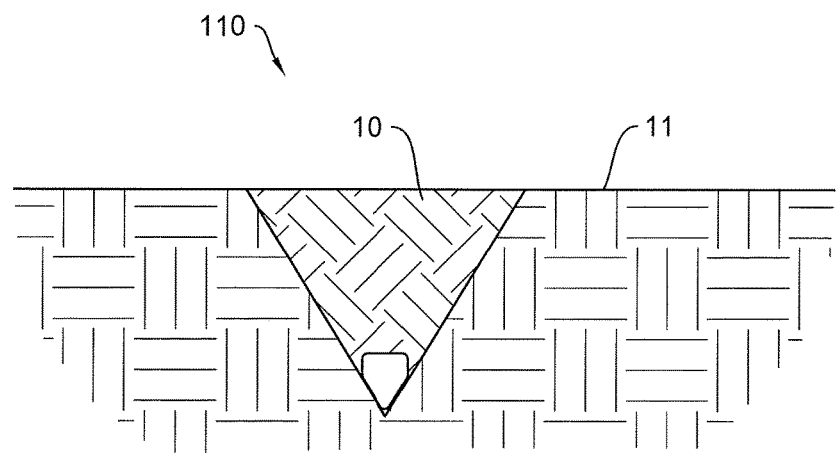
FIG. 6 is a representative example of a work layer image generated by the work layer sensor of FIG. 5.

FIG. 6 is a representative illustration of the work layer image 110 generated by the work layer sensor 100-3 of FIG. 5 which provides a view not only of the seed trench but also a portion of the soil adjacent to each side of the seed trench.

For each of the work layer sensor embodiments 100-1, 100-2, 100-3, the frequency of operation of the work layer sensors 100 and the vertical position of the transmitters (T) and receivers (R) above the soil and the spacing between the transmitters (T) and receivers (R) are selected to minimize signal to noise ratio while also capturing the desired depth and width of the soil region of interest (the work layer 104) for which the work layer image 110 is generated.

Planter Applications

Figure 7:
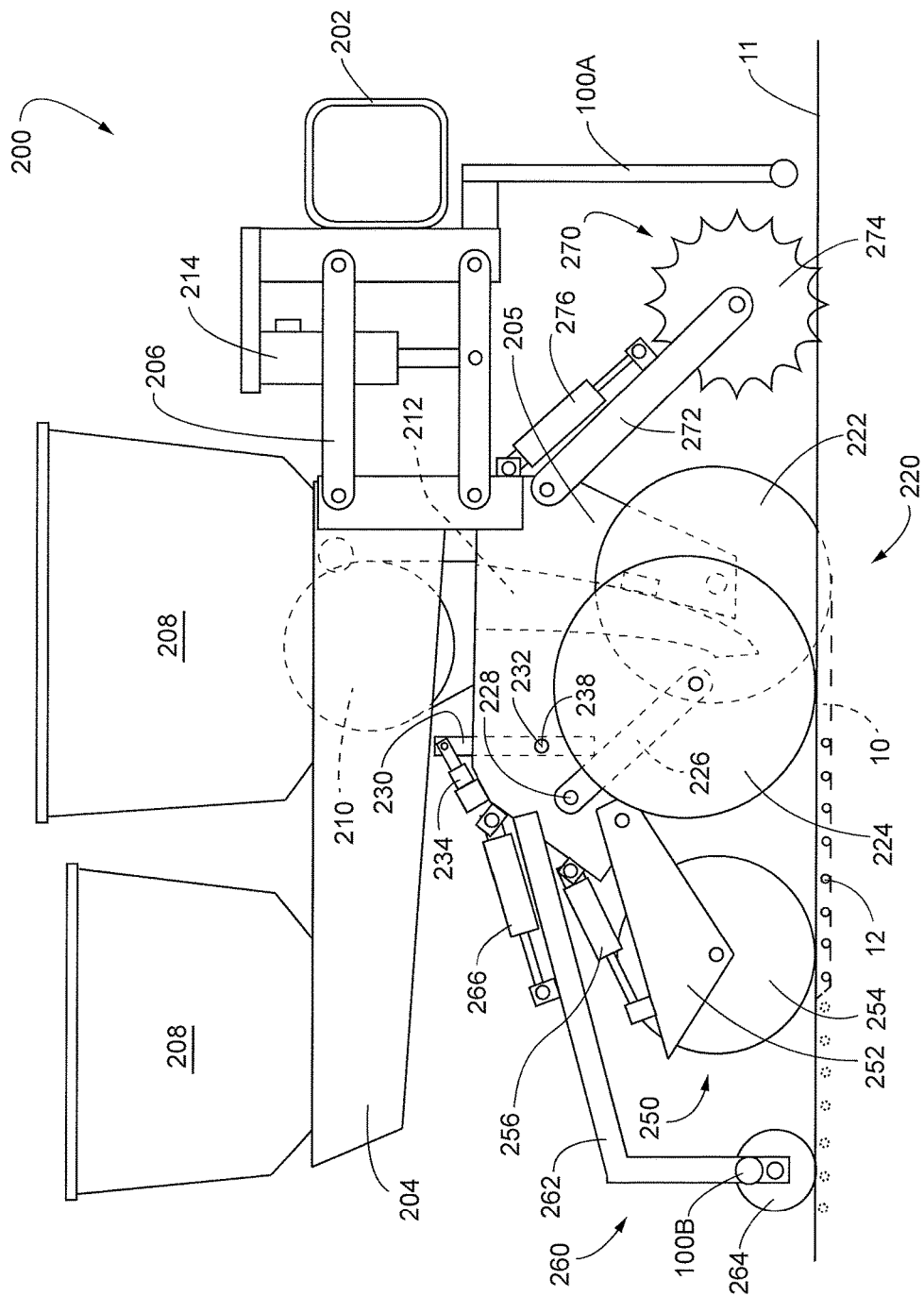
FIG. 7 is a side elevation view of an embodiment of a row unit of an agricultural planter incorporating a work layer sensor of FIG. 1, 3 or 5.

FIG. 7 illustrates one example of a particular application of the work layer sensors 100 disposed on a row unit 200 of an agricultural planter. The row unit 200 includes a work layer sensor 100A disposed on a forward end of the row unit 200 and a work layer sensor 100B disposed rearward end of the row unit 200. The forward and rearward work layer sensors 100A, 100B may comprise any of the embodiments of the work layer sensors 100-1, 100-2, 100-3 previously described.

The forward work layer sensor 100A is disposed to generate a reference work layer image (hereinafter a "reference layer image") 110A of the soil prior to the soil being disturbed by the planter, whereas the rearward work layer sensor 100B generates the work layer image 110B, which in this example, is the image of the closed seed trench 10 in which the seed has been deposited and covered with soil. For the reasons explained later, it is desirable to obtain both a reference image 110A and the work layer image 110B for analysis of the soil characteristics through the work layer 104.

It should be appreciated that the forward and rearward work layer sensors 100A, 100B referenced in FIG. 7 may employ any of the embodiments 100-1, 100-2 or 100-3 previously described. However, it should be appreciated that if the embodiments 100-2 or 100-3 are employed, the forward work layer sensor 100A may be eliminated because the embodiments 100-2 and 100-3 are configured to generate the work layer images 110 of undisturbed soil adjacent to the seed trench 10 which could serve as the reference layer image 110A.

With respect to FIG. 7, the row unit 200 is comprised of a frame 204 pivotally connected to the toolbar 202 by a parallel linkage 206 enabling each row unit 200 to move vertically independently of the toolbar 202. The frame 204 operably supports one or more hoppers 208, a seed meter 210, a seed delivery mechanism 212, a downforce control system 214, a seed trench opening assembly 220, a trench closing assembly 250, a packer wheel assembly 260, and a row cleaner assembly 270. It should be understood that the row unit 200 shown in FIG. 7 may be for a conventional planter or the row unit 200 may be a central fill planter, in which case the hoppers 208 may be replaced with one or more mini-hoppers and the frame 204 modified accordingly as would be recognized by those of skill in the art.

The downforce control system 214 is disposed to apply lift and/or downforce on the row unit 200 such as disclosed in U.S. Publication No. US2014/0090585, which is incorporated herein in its entirety by reference.

The seed trench opening assembly 220 includes a pair of opening discs 222 rotatably supported by a downwardly extending shank member 205 of the frame 204. The opening discs 222 are arranged to diverge outwardly and rearwardly so as to open a v-shaped trench 10 in the soil 11 as the planter traverses the field. The seed delivery mechanism 212, such as a seed tube or seed conveyor, is positioned between the opening discs 222 to deliver seed from the seed meter 210 and deposit it into the opened seed trench 10. The depth of the seed trench 10 is controlled by a pair of gauge wheels 224 positioned adjacent to the opening discs 222. The gauge wheels 224 are rotatably supported by gauge wheel arms 226 which are pivotally secured at one end to the frame 204 about pivot pin 228. A rocker arm 230 is pivotally supported on the frame 204 by a pivot pin 232. It should be appreciated that rotation of the rocker arm 230 about the pivot pin 232 sets the depth of the trench 10 by limiting the upward travel of the gauge wheel arms 226 (and thus the gauge wheels) relative to the opening discs 222. The rocker arm 230 may be adjustably positioned via a linear actuator 234 mounted to the row unit frame 204 and pivotally coupled to an upper end of the rocker arm 230. The linear actuator 234 may be controlled remotely or automatically actuated as disclosed, for example, in International Publication No. WO2014/186810, which is incorporated herein in its entirety by reference.

A downforce sensor 238 is configured to generate a signal related to the amount of force imposed by the gauge wheels 224 on the soil. In some embodiments the pivot pin 232 for the rocker arm 230 may comprise the downforce sensor 238, such as the instrumented pins disclosed in U.S. Pat. No. 8,561,472, which is incorporated herein in its entirety by reference.

The seed meter 210 may be any commercially available seed meter, such as the finger-type meter or vacuum seed meter, such as the VSet® meter, available from Precision Planting LLC, 23207 Townline Rd, Tremont, Ill. 61568.

The trench closing assembly 250 includes a closing wheel arm 252 which pivotally attaches to the row unit frame 204. A pair of offset closing wheels 254 are rotatably attached to the closing wheel arm 252 and angularly disposed to direct soil back into the open seed trench so as to "close" the soil trench. An actuator 256 may be pivotally attached at one end to the closing wheel arm 252 and at its other end to the row unit frame 204 to vary the down pressure exerted by the closing wheels 254 depending on soil conditions. The closing wheel assembly 250 may be of the type disclosed in International Publication No. WO2014/066650, which is incorporated herein in its entirety by reference.

The packer wheel assembly 260 comprises an arm 262 pivotally attached to the row unit fame 204 and extends rearward of the closing wheel assembly 250 and in alignment therewith. The arm 262 rotatably supports a packer wheel 264. An actuator 266 is pivotally attached at one end to the arm and at its other end to the row unit frame 204 to vary the amount of downforce exerted by the packer wheel 264 to pack the soil over the seed trench 10.

The row cleaner assembly 270 may be the CleanSweep® system available from Precision Planting LLC, 23207 Townline Rd, Tremont, Ill. 61568. The row cleaner assembly 270 includes an arm 272 pivotally attached to the forward end of the row unit frame 204 and aligned with the trench opening assembly 220. A pair of row cleaner wheels 274 are rotatably attached to the forward end of the arm 272. An actuator 276 is pivotally attached at one end to the arm 272 and at its other end to the row unit frame 204 to adjust the downforce on the arm to vary the aggressiveness of the action of the row cleaning wheels 274 depending on the amount of crop residue and soil conditions.

It should be appreciated that rather than positioning the work layer sensors 100 as shown in FIG. 7, the work layer sensors may be positioned after the row cleaner assembly 270 and before the trench opening assembly 220 or in one or more other locations between the trench opening discs 222 and the closing wheels 254 or the packing wheel 264 depending on the soil region or characteristics of interest.

Planter Control and Operator Feedback

Figure 8:
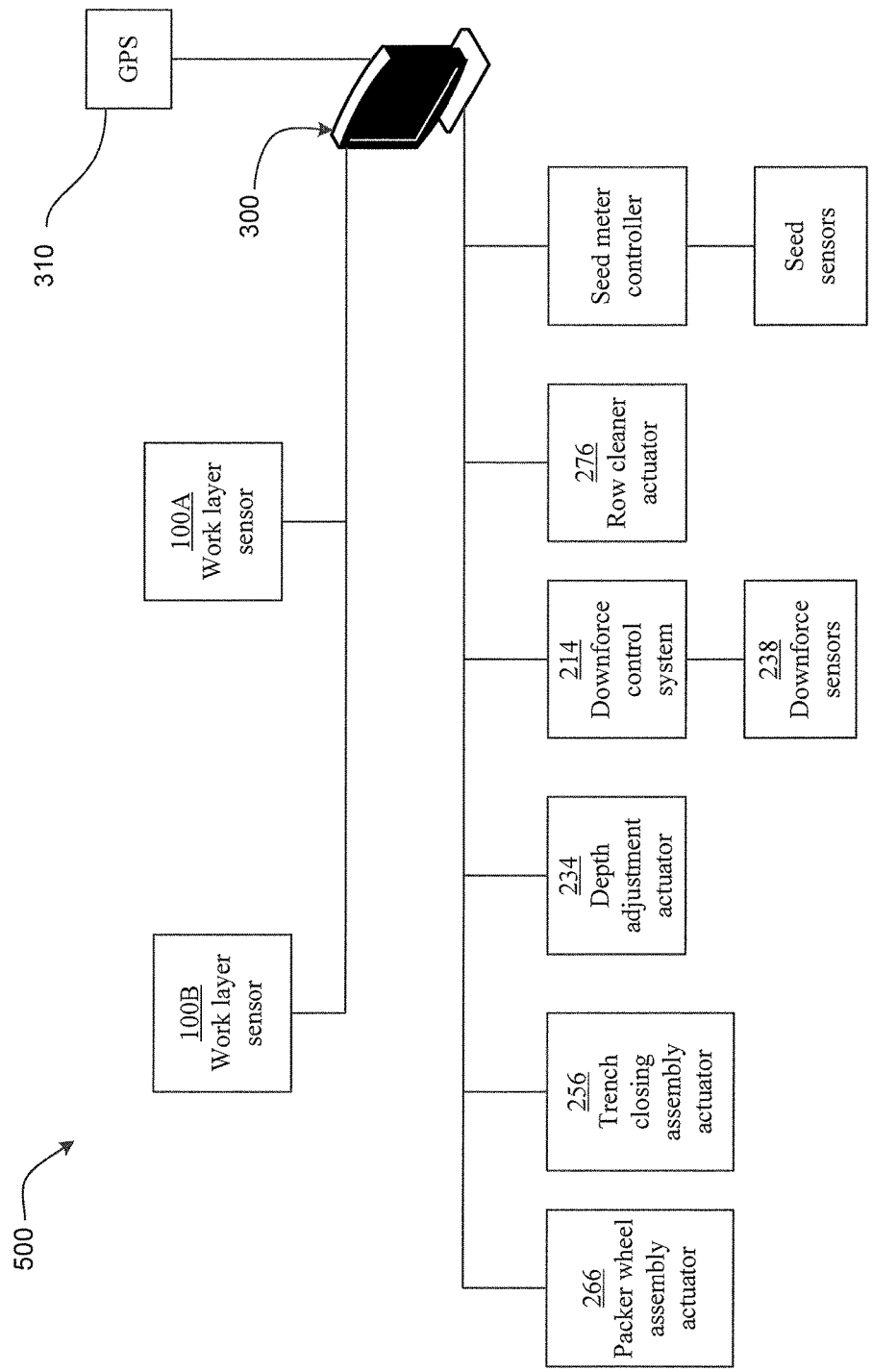
FIG. 8 illustrates an embodiment of a work layer implement monitoring, control and operator feedback system.

FIG. 8 is a schematic illustration of a system 500 which employs work layer sensors 100 to provide operator feedback and to control the planter row unit 200. Work layer sensors 100A, 100B are disposed to generate a reference layer image 110A of undisturbed soil and a work layer image 110B of the closed seed trench (i.e., after seed is deposited, covered with soil by the closing wheel assembly 250 and the soil packed with the packing wheel assembly 260). As previously described, the work layer sensors 100A, 100B may be separate work layer sensors disposed forward and rearward of the row unit 200 as illustrated in FIG. 7, or the work layer sensors 100A, 100B may comprise a single work layer sensor with transmitters (T) and receivers (R) disposed to generate both a reference layer image 110A and a work layer image 110B.

The work layer image 110B may be communicated and displayed to the operator on a monitor 300 comprising a display, a controller and user interface such as a graphical user interface (GUI), within the cab of the tractor.

The monitor 300 may be in signal communication with a GPS unit 310, the row cleaner actuator 276, the downforce control system 214, the depth adjustment actuator 234, the trench closing assembly actuator 256 and the packer wheel assembly actuator 266 to enable operational control of the planter based on the characteristics of the work layer image 110B.

For example, if the work layer image 110B indicates that residue in the seed trench 10 is above a predetermined threshold (as explained below), a signal is generated by the monitor 300 to actuate the row cleaner actuator 276 to increase row cleaner downforce. As another example, if the seed depth is less than a predetermined threshold (as explained below), a signal is generated by the monitor 300 to actuate the downforce control system 214 to increase the downforce and/or to actuate the depth adjustment actuator 234 to adjust the gauge wheels 234 relative to the opening discs 232 to increase the trench depth. Likewise if the seed depth is greater than a predetermined threshold, a signal is generated by the monitor 300 to actuate the downforce control system 214 to decrease the downforce and/or to actuate the depth adjustment actuator 234 to decrease the trench depth. As another example, if the upper portion of the trench has more than a threshold level of void space (as explained below), a signal is generated by the monitor 300 to actuate the trench closing wheel assembly actuator 256 to increase the downforce on the closing wheels 254. As another example, if the lower portion of the trench has more than a threshold level of void space (as explained below), a signal is generated by the monitor 300 to actuate the packer wheel assembly actuator 266 to increase the downforce on the packer wheel 264.

In still other examples, the work layer image 110B may identify and/or analyze (e.g., determine depth, area, volume, density or other qualities or quantities of) subterranean features of interest such as tile lines, large rocks, or compaction layers resulting from tillage and other field traffic. Such subterranean features may be displayed to the user on the monitor 300 and/or identified by the monitor 300 using an empirical correlation between image properties and a set of subterranean features expected to be encountered in the field. In one such example, the area traversed by the gauge wheels (or other wheels) of the planter (or tractor or other implement or vehicle) may be analyzed to determine a depth and/or soil density of a compaction layer beneath the wheels. In some such examples, the area of the work layer image may be divided into sub-regions for analysis based on anticipated subterranean features in such sub-regions (e.g., the area traversed by the gauge wheels may be analyzed for compaction).

In other examples, the monitor 300 may estimate a soil property (e.g., soil moisture, organic matter, or electrical conductivity, water table level) based on image properties of the work layer image 110B and display the soil property to the user as a numerical (e.g., average or current) value or a spatial map of the soil property at geo-referenced locations in the field associated with each soil property measurement (e.g., by correlating measurements with concurrent geo-referenced locations reported the GPS unit 310).

Alternatively or additionally, the monitor 300 could be programmed to display operational recommendations based on the characteristics of the work layer image 110B. For example, if the work layer image 110B identifies that the seed 12 is irregularly spaced in the trench 10 or if the seed 12 is not being uniformly deposited in the base of the trench, or if the spacing of the seed 12 in the trench does not match the anticipated spacing of the seed based on the signals generated by the seed sensor or speed of the seed meter, such irregular spacing, non-uniform positioning or other inconsistencies with anticipated spacing may be due to excess speed causing seed bounce within the trench or excess vertical acceleration of the row unit. As such, the monitor 300 may be programmed to recommend decreasing the planting speed or to suggest increasing downforce (if not automatically controlled as previously described) to reduce vertical acceleration of the planter row units. Likewise to the extent the other actuators 276, 214, 234, 256, 266 are not integrated with the monitor controller, the monitor may be programmed to display recommendations to the operator to make manual or remote adjustments as previously described based on the characteristics of the work layer image 110B.

Figure 9:
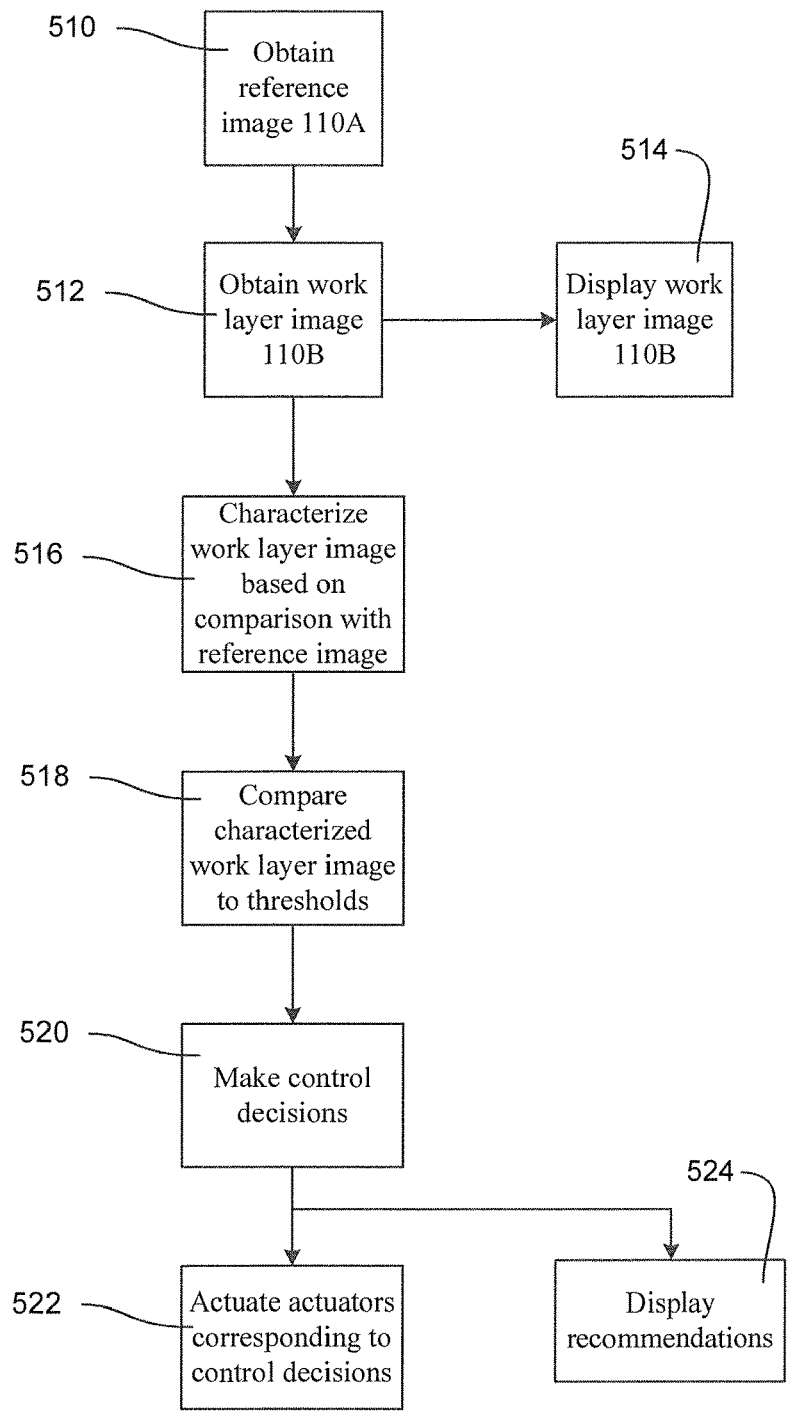
FIG. 9 is a chart showing a process for work layer implement monitoring, control and operator feedback.

FIG. 9 illustrates the process steps for controlling the planter and providing operator feedback. At steps 510 and 512, the reference image 110A and work layer image 110B is generated by the work image sensor(s) 100. At step 514, the work layer image 110B may be displayed to the operator on the monitor 300 in the cab of the tractor. At step 516, the reference layer image 110A is compared with the work layer image 110B to characterize the work layer image. At step 518, the characterized work layer image 110B is compared to predetermined thresholds. At step 520, control decisions are made based on the comparison of the characterized work layer image 110B with the predetermined thresholds. At step 522, the planter components may be controlled by the monitor 300 generating signals to actuate one or more of the corresponding actuators 276, 214, 234, 256, 266 and/or at step 524, corresponding recommendations may be displayed to the operator on the monitor display.

To characterize the work layer image 110B at step 516, the monitor 300 compares one or more characteristics (e.g., density) of the reference image 110A with the same characteristics of the work layer image 110B. In some embodiments, a characterized image may be generated comprising only portions of the work layer image differing from the reference image by at least a threshold value. The characterized image may then be used to identify and define features of the work layer image 110B, such as the trench shape, the trench depth, residue in the trench, seeds and seed placement within the trench, void spaces within the trench, and density differences of the soil within the trench.

For example, to determine the seed depth, the seed is identified or identifiable from the work layer image 110B by determining regions within the work layer image having a size or shape corresponding to a seed and having a density range empirically corresponding to seed. Once a region is identified as a seed, the vertical position of the seed with respect to the soil surface is readily measurable or determined.

As another example, the amount of residue in the trench can be determined by (a) defining the area of the trench cross-section (based on soil density differences between the reference image 110A and the work layer image 110B); (b) by identifying the regions within the trench having a density range empirically corresponding to residue; (c) totaling the area of the regions corresponding to residue; and (d) dividing the residue area by the trench cross-sectional area.

Other Applications

It should be appreciated that work layer sensors 100 may be employed with other agricultural implements and operations, such as, for example, tillage operations and/or sidedress fertilization operations, or in connection with agricultural data gathering operations to view or analyze below-surface soil characteristics, seed placement, root structure, location of underground water-management features such as tiling, etc.

When employed with tillage implements, the work layer sensors 100 may be disposed forward of any tillage tools (i.e., shank, disk, blade, knife, spoon, coulter, etc.) or between forward and rearward spaced tillage tools and/or rearward of any tillage tools.

When employed with sidedress or other in-ground fertilization tools, the work layer sensors 100 may be disposed forward or rearward of any sidedress or in-ground tools (i.e., shank, disk, blade, knife, spoon, coulter, leveling basket harrows, etc.).

When employed with a dedicated measurement implement, the work layer sensors 100 may be disposed above undisturbed soil which may or may not have residue cleared by a row cleaner.

For the tillage implements and sidedress or in-ground fertilization tools, actuators on these implements can be automatically controlled to adjust depth of the tillage tools or the monitor 300 can be programmed to provide feedback or recommendations to the operator to manually adjust or remotely adjust the actuators as described above with respect to the planter application. For example, if the feedback or recommendations to the operator indicate that the depth of the tillage tools should be adjusted, an actuator associated with ground engaging wheels supporting the toolbar or a section of the toolbar may be actuated to raise or lower the toolbar to decrease or increase the depth of penetration of the toolbars. Alternatively, separate actuators may be associated with individual tillage tools to adjust the depth of the individual tillage tools. As another example, if the work layer images indicate that the implement is approaching more dense or compact soil, actuators associated to adjust downforce or pressure may be actuated to increase the downforce as the implement passes through the more dense or compact soil. In other embodiments if the work layer images across the width of the implement indicate that one side or the other is tilling the soil more aggressively, an actuator associated with a wing of the implement may be actuated to ensure balancing of the aggressiveness of tillage tools across the side-to-side width of the implement. Likewise an actuator associated with fore and aft leveling of the implement may be actuated to ensure aggressiveness of tools on the front of the implement are balanced with those on the back. In still other embodiments, actuators may be provided to adjust the angle of attack of a disc gang or wing of a tillage implement, or individual tillage tools depending on the work layer images and operator feedback as the implement traverses the field encountering different soil conditions.

The foregoing description is presented to enable one of ordinary skill in the art to make and use the invention and is provided in the context of a patent application and its requirements. Various modifications to the preferred embodiment of the apparatus, and the general principles and features of the system and methods described herein will be readily apparent to those of skill in the art. Thus, the present invention is not to be limited to the embodiments of the apparatus, system and methods described above and illustrated in the drawing figures, but is to be accorded the widest scope consistent with the spirit and scope of the appended claims.

The invention claimed is:

1. A soil imaging system, comprising:
at least one work layer sensor disposed on an agricultural implement traveling in a forward direction of travel while performing a soil working operation, the at least one work layer sensor disposed at or behind the agricultural implement to generate an electromagnetic field through a soil layer of interest as or after the soil layer has been worked by the soil working operation;
a monitor in communication with the work layer sensor and adapted to generate a work layer image of the soil layer of interest based on the generated electromagnetic field through the soil layer of interest as or after the soil has been worked by the soil working operation,
wherein the monitor generates a reference image based on an electromagnetic field generated through the undisturbed soil,
wherein the monitor compares at least one characteristic of the reference image with at least one characteristic of the work layer image and generates a characterized image of the soil layer of interest.

2. The soil imaging system of claim 1 wherein the monitor estimates a soil property based on the work layer image.

3. The soil imaging system of claim 2 wherein the monitor displays the estimated soil property as a numerical value associated with a geo-referenced location in the field to define a spatial map of the field based on the estimated soil properties.

4. The soil imaging system of claim 2, wherein the at least one work layer sensor is disposed on a row unit of an agricultural planter in relation to a seed trench formed by the row unit and wherein the work layer sensor generates a work layer image of the seed trench.

5. The soil imaging system of claim 4, wherein the at least one work layer sensor generates the electromagnetic field through undisturbed soil outside of the seed trench.

6. The soil imaging system of claim 5, wherein the monitor compares at least one characteristic of the reference image with at least one characteristic of the work layer image and generates a characterized image of the seed trench.

7. The soil imaging system of claim 6, wherein the characterized image identifies the seed trench shape.

8. The soil imaging system of claim 6, wherein the characterized image identifies the seed trench depth.

9. The soil imaging system of claim 8, wherein the characterized image identifies depth of seed deposited in the seed trench relative to the trench depth.

10. The soil imaging system of claim 9, wherein if the characterized image identifies seed depth is less than a predetermined threshold, the monitor generates a signal to actuate a downforce control actuator on the planter row unit to increase the downforce.

11. The soil imaging system of claim 9, wherein if the characterized image identifies seed depth is less than a predetermined threshold, the monitor generates a signal to actuate a depth adjustment actuator on the planter row unit to increase the trench depth.

12. The soil imaging system of claim 6, wherein the characterized image identifies crop residue in the seed trench.

13. The soil imaging system of claim 12, wherein if the characterized image identifies that crop residue in the seed trench is above a predetermined threshold, the monitor generates a signal to actuate a row cleaner actuator on the planter row unit to increase row cleaner downforce.

14. The soil imaging system of claim 6, wherein the characterized image identifies void spaces within the seed trench.

15. The soil imaging system of claim 14, wherein if the characterized image identifies that an upper portion of the seed trench has more than a threshold level of void space, the monitor generates a signal to actuate a trench closing wheel assembly actuator on the planter row unit to increase downforce of the closing wheel assembly.

16. The soil imaging system of claim 6, wherein the monitor determines seed-to-soil contact based on the characterized image.

17. The soil imaging system of claim 6, wherein the monitor determines a percentage closed of the seed trench based on the characterized image.

18. The soil imaging system of claim 6, wherein the monitor determines a percentage of upper portion closed of the seed trench based on the characterized image.

19. The soil imaging system of claim 18, wherein if the characterized image identifies that a lower portion of the seed trench has more than a threshold level of void space, the monitor generates a signal to actuate a packer wheel assembly actuator on the planter row unit to increase downforce on the packer wheel.

20. The soil imaging system of claim 6, wherein the monitor determines a percentage of lower portion closed of the seed trench based on the characterized image.

21. The soil imaging system of claim 5, wherein the at least one work layer sensor comprises a transmitter disposed on one side of the seed trench, a first receiver disposed on the other side of the seed trench to generate the work layer image of the seed trench, and a second receiver is disposed adjacent and rearward of the transmitter to produce the reference image outside of the seed trench.

22. The soil imaging system of claim 5, wherein the at least one work layer sensor comprises a plurality of transmitter and receiver pairs disposed above and transverse to the seed trench, wherein the transmitter and receiver pairs disposed above the seed trench generate the work layer image of the seed trench, and the transmitter and receiver pairs disposed transverse to the seed trench produce the reference image outside of the seed trench.

23. The soil imaging system of claim 4, wherein the at least one work layer sensor comprises a transmitter disposed on one side of the seed trench and a receiver disposed on the other side of the seed trench to generate the work layer image of the seed trench.

24. The soil imaging system of claim 1, further comprising at least one reference sensor generating the electromagnetic field through undisturbed soil ahead of the agricultural implement while traveling in the forward direction of travel.

25. The soil imaging system of claim 24, wherein the monitor compares at least one characteristic of the reference image with at least one characteristic of the work layer image and generates a characterized image of a work layer of interest.

26. The soil imaging system of claim 25, wherein the monitor displays operator feedback based on the characterized image.

27. The soil imaging system of claim 25, wherein the monitor effects operational control of the agricultural implement based on the characterized image.

28. The soil imaging system of claim 1, wherein the soil working operation is one of seed planting, tillage, sidedress, or in-ground fertilization.

29. A soil imaging system, comprising:
   a toolbar comprising at least one agricultural implement, the at least one agricultural implement performing at least one soil working operation;
   at least one work layer sensor disposed adjacent to the at least one agricultural implement, the work layer sensor generating an electromagnetic field through a soil layer of interest as the agricultural implement traverses a field;
   a monitor in communication with the work layer sensor and adapted to generate a work layer image of the soil layer of interest based on the generated electromagnetic field through the soil layer of interest as the agricultural implement traverses the field,
   wherein the monitor generates a reference image based on an electromagnetic field generated through the undisturbed soil,
   wherein the monitor compares at least one characteristic of the reference image with at least one characteristic of the work layer image and generates a characterized image of the soil layer of interest.

30. The soil imaging system of claim 29, wherein there is a work layer sensor disposed adjacent to each agricultural implement.

31. The soil imaging system of claim 30, wherein the work layer sensor is at or behind each agricultural implement.

* * * * *